(12) United States Patent
Taniguchi et al.

(10) Patent No.: US 7,847,928 B2
(45) Date of Patent: Dec. 7, 2010

(54) INSPECTION DEVICE AND INSPECTION METHOD

(75) Inventors: Koichi Taniguchi, Hitachinaka (JP); Masayuki Ochi, Kamisato (JP); Shuichi Chikamatsu, Kounosu (JP); Shigehisa Nozawa, Kamisato (JP)

(73) Assignee: Hitachi High-Technologies Corporation, Tokyo (JP)

( * ) Notice: Subject to any disclaimer, the term of this patent is extended or adjusted under 35 U.S.C. 154(b) by 348 days.

(21) Appl. No.: 12/130,488

(22) Filed: May 30, 2008

(65) Prior Publication Data

US 2008/0297779 A1 Dec. 4, 2008

(30) Foreign Application Priority Data

May 31, 2007 (JP) .............................. 2007-145783

(51) Int. Cl.
G01N 21/00 (2006.01)
(52) U.S. Cl. .................................. 356/237.4; 356/237.3
(58) Field of Classification Search ... 356/237.2–237.6; 382/298–299
See application file for complete search history.

(56) References Cited

U.S. PATENT DOCUMENTS 6,271,933 B1 8/2001 Asai et al.

2006/0203231 A1 9/2006 Uto et al.

FOREIGN PATENT DOCUMENTS

| JP | 4-362790 | 12/1992 |
|---|---|---|
| JP | 10-224529 | 8/1998 |
| JP | 2003-346698 | 12/2003 |
| JP | 2005-201782 | 7/2005 |
| JP | 2006-250739 | 9/2006 |

*Primary Examiner*—Gregory J Toatley
*Assistant Examiner*—Tri T Ton
(74) *Attorney, Agent, or Firm*—Mcdermott Will & Emery LLP

(57) ABSTRACT

An inspection device for inspecting defects of an inspection object including a light source for irradiating a luminous flux to the inspection object; an optical system for guiding reflected light from the inspection object; a photoelectric image sensor having a plurality of photoelectric cells arranged, for converting the light guided to detection signals; a detection signal transfer unit having channels each constituted by a signal correction unit, a converter and an image formation unit, and corresponding to each of a plurality of regions formed by dividing the photoelectric image sensor, respectively; and an image synthesis unit for forming an image of the surface of the object by synthesizing partial images outputted; the inspection device inspecting defects of the object by processing the synthesized image; whereby it becomes possible to correct a detection signal from said photoelectric cell close to a predetermined reference target value.

16 Claims, 5 Drawing Sheets

INSPECTION DEVICE AND INSPECTION METHOD

BACKGROUND OF THE INVENTION

1. Field of the Invention

This invention relates to an inspection device for inspecting defective images and adhering foreign matters of an inspection object on which images are formed, such as a wafer, a liquid crystal panel, a mask, and so forth, and an inspection method for this inspection device.

2. Description of the Related Art

In a semiconductor production process, for example, foreign matters existing on a semiconductor substrate or pattern defects created during the production process cause defects such as inferior insulation and short-circuit and lower a production yield. Smaller foreign matters or defects, if any, may result in a critical problem with further miniaturization of semiconductor devices and more delicate defect detection becomes therefore necessary.

The defects and the foreign matters are detected in an early stage of a production process by using a semiconductor inspection device on a semiconductor production line, for example, and the causes of the defects are specified and are fed back to the production process so as to improve the production yield.

However, an equivalent inspection sensitivity cannot always be obtained by an inspection device of the same type and even when the same inspection object is inspected, differences often occur in the number and kind of defects detected.

To reduce the inspection sensitivity difference (machine difference) among the inspection devices (machines), it is import to conduct adjustment of the inspection sensitivity and to keep conformity but it is practically difficult to render the inspection sensitivity of the inspection devices (machines) uniform owing to variance of performances of elements that constitute the inspection device (machine). Therefore, a correction method for reducing the variance has been required.

JP-A-2005-201782 as one of the prior art technologies of this kind discloses a technology for reducing noise resulting from a detection system by combining a plurality of sensors and correcting signals.

JP-A-2003-346698 describes a method for correcting influences of fluctuation resulting from non-uniformity of electron beam dosage and time by using a plurality of detectors in an electron beam apparatus and individually executing gain correction and offset correction for each of the detectors.

The reference described above, i.e. JP-A-2003-346698, describes also a method for correcting non-uniformity of signal intensity inside a visual field by dividing a two-dimensional sensor into a plurality of regions and correcting a digital level of an output signal for each of the regions divided.

Another reference JP-A-4-362790 discloses a method for correcting light power fluctuation by an exposure time in a scan type sensor.

Still another reference JP-A-2006-250739 describes illumination light correction in an illumination optical system by changing a shape of a reflecting surface to execute aberration correction.

SUMMARY OF THE INVENTION

The prior art technologies described above can adjust the inspection sensitivity or the image formation sensitivity by making uniform the levels of the individual detection signals of each inspection device (machine), it is true, but do not take into consideration how to keep conformity of the inspection sensitivity among the respective inspection devices (machines).

When a light source the illumination intensity distribution of which is not uniform inside an inspection visual field but which has a plane-like distribution is used, a noise level will increase when a detection signal of an inspection region having different illumination intensity is deliberately increased and the inspection sensitivity cannot be always improved.

It is therefore an object of the invention to provide an inspection device that can reduce an inspection device (machine) difference of output signals from a photoelectric image sensor owing to variance of optical performance of each inspection device (machine) and can keep conformity of inspection sensitivity, and an inspection method for the inspection device.

It is another object of the invention to reduce a machine difference of inspection sensitivity among a plurality of inspection devices (machines) resulting from variance of performances of constituent elements such as an illumination system having a light source, an optical system for guiding reflected and scattered light, a detection system having a photoelectric image sensor, and so forth, by correcting detection signals from the detection system.

According to one aspect of the invention, there is provided an inspection device for inspecting defects or foreign matters on a surface of an inspection object, including a light source for irradiating a luminous flux to the inspection object; an optical system for guiding reflected and scattered light reflected from the inspection object; a photoelectric image sensor having a plurality of photoelectric cells arranged, for converting the reflected and scattered light guided to electric detection signals; a detection signal transfer unit having channels each constituted by a signal correction unit, an A/D converter and an image formation unit, and corresponding to each of a plurality of regions formed by dividing the photoelectric image sensor, respectively; and an image synthesis unit for forming an image of the surface of the inspection object by synthesizing partial images outputted by the detection signal transfer unit; the inspection device inspecting defects or foreign matters of the surface of the inspection object by processing the synthesized image; wherein the detection signal transfer unit has a detection signal correction function capable of bringing a detection signal from the photoelectric cell close to a reference target value of a reference detection signal intensity determined for each of the channels.

The detection system of the photoelectric sensor has light reception elements (photoelectric cells) that are arranged either one-dimensionally or two-dimensionally and has channels (detection signal transfer unit) for transferring a detection signal to each photoelectric cell.

The detection signal transfer unit having a plurality of channels is constituted in such a fashion as to be capable of individually correcting the detection signals for each channel.

The inspection device according to the invention further includes an external input unit for sharing a correction target value (correction coefficient) as a correction target of the detection signal among a plurality of machines.

The invention can execute correction in such a fashion as to bring the detection signal from each photoelectric cell close to the reference target value of the reference detection signal determined for each channel. Therefore, the invention can reduce the inspection sensitivity difference resulting from variance of performance of constituent elements of a plurality of inspection devices and can achieve equivalent inspection sensitivity among a plurality of inspection devices (machines). The invention can further correct easily the change of the detection signal owing to the change with time of the light source and the cells and can conduct stable inspection.

The invention will be hereinafter described in further detail with reference to the accompanying drawings.

DESCRIPTION OF THE EMBODIMENTS

Embodiment 1

Figure 1:
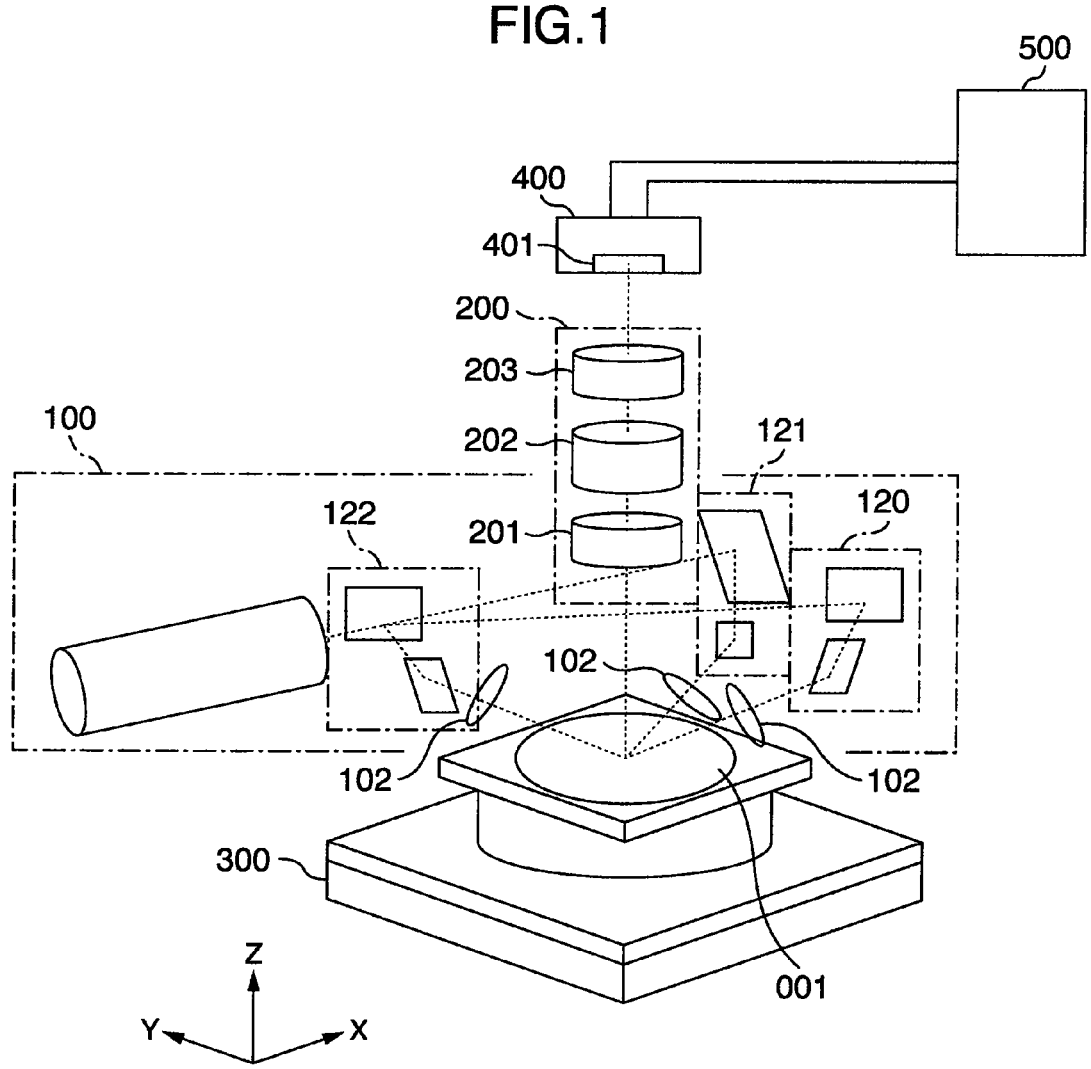
FIG. 1 shows a schematic construction of an inspection device according to an embodiment of the present invention.

An inspection device for inspecting a defect according to the invention will be explained with reference to FIG. 1.

The inspection device for inspecting a defect includes a stage 300 for supporting thereon an inspection object 001 to be inspected and an illumination optical system 100 having a laser light source 101, a beam shaping unit 102 and a plurality of irradiation units 120, 121 and 122 branched by an optical path branching/switching optical system.

This illumination optical system 100 irradiates a luminous flux of a light source (laser light source 101) to the test piece.

The inspection device for inspecting a defect further includes a condensation optical system 200 having an objective lens 201, a zoom lens group 202 and an imaging lens 203.

The condensation optical system 200 guides reflected and scattered light reflected from the inspection object to a detection system to be described later.

The inspection device for inspecting a defect further includes a detection system 400 having a light reception surface 401 which has light reception devices arranged either one-dimensionally or two-dimensionally and which is divided into a plurality of regions, a channel group 501 for transferring a detection signal from the detection system to each region and an image processing system 500 for processing the detection signal 400 and executing defect judgment.

The channel group 501 operates as a detection signal transfer unit and has a correction function of correcting the intensity of the detection signal as will be later described.

Figure 2:
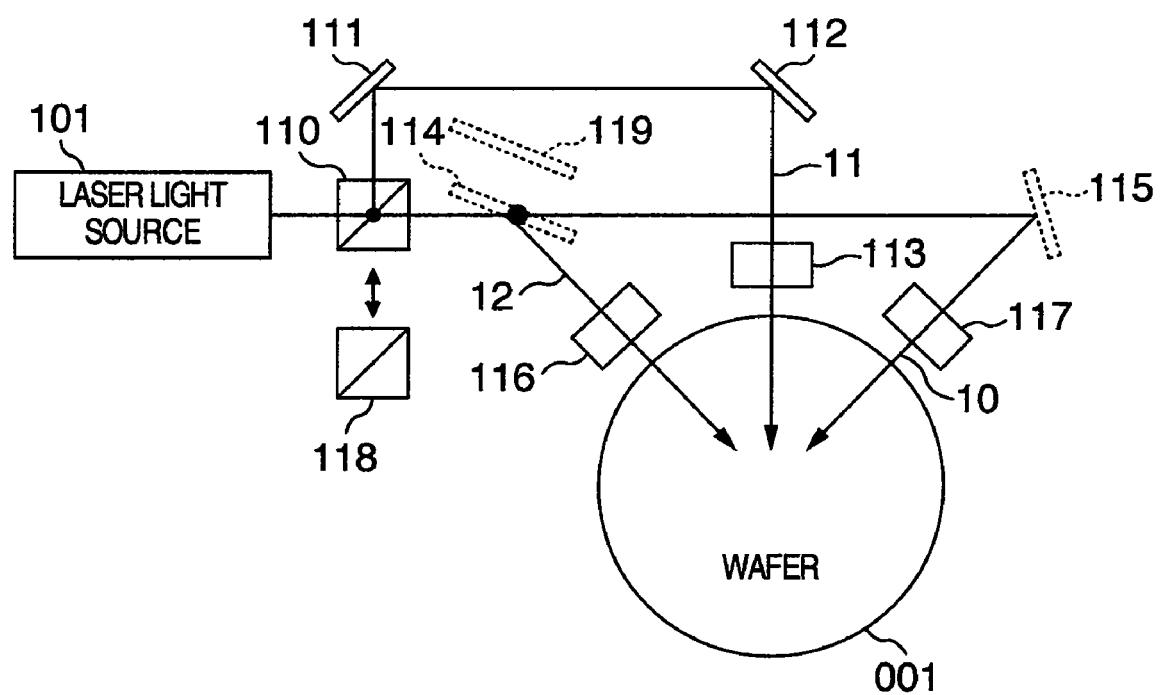
FIG. 2 is a plan view of an illumination optical system 100 in the embodiment of the invention.

FIG. 2 is a plan view of the illumination optical system 100 for irradiating illumination light to the inspection object from three directions.

A laser beam outgoing from the laser light source 101 is branched to two optical paths by a branching optical device 110. One of the optical paths is reflected by mirrors 111 and 112 and is allowed to be incident downward to the beam shaping unit 102 by a mirror 113 to give illumination light from a direction 11. The other travels towards a branching optical device 114 such as a half mirror.

One of the optical paths branched by the branching optical device 114 is reflected by a mirror 115 and is allowed to be incident downward to the beam shaping unit 102 by a mirror 1137 to give an illumination beam from a direction 10. The other is allowed to be incident downward to the beam shaping unit 102 by a mirror 116 to give illumination light from a direction 12.

Incidentally, when illumination is made from only the direction 11, illumination can be achieved by switching from the branching optical device 110 to a mirror device 118.

When illumination is made from two directions 10 and 12, illumination can be achieved by removing the optical branching device 110 from the optical path or changing it to a pass-through optical device.

When illumination is made from only the direction 12 of the two directions 10 and 12, for example, illumination can be achieved by changing the branching optical device 114 to a mirror device 119.

Figure 3:
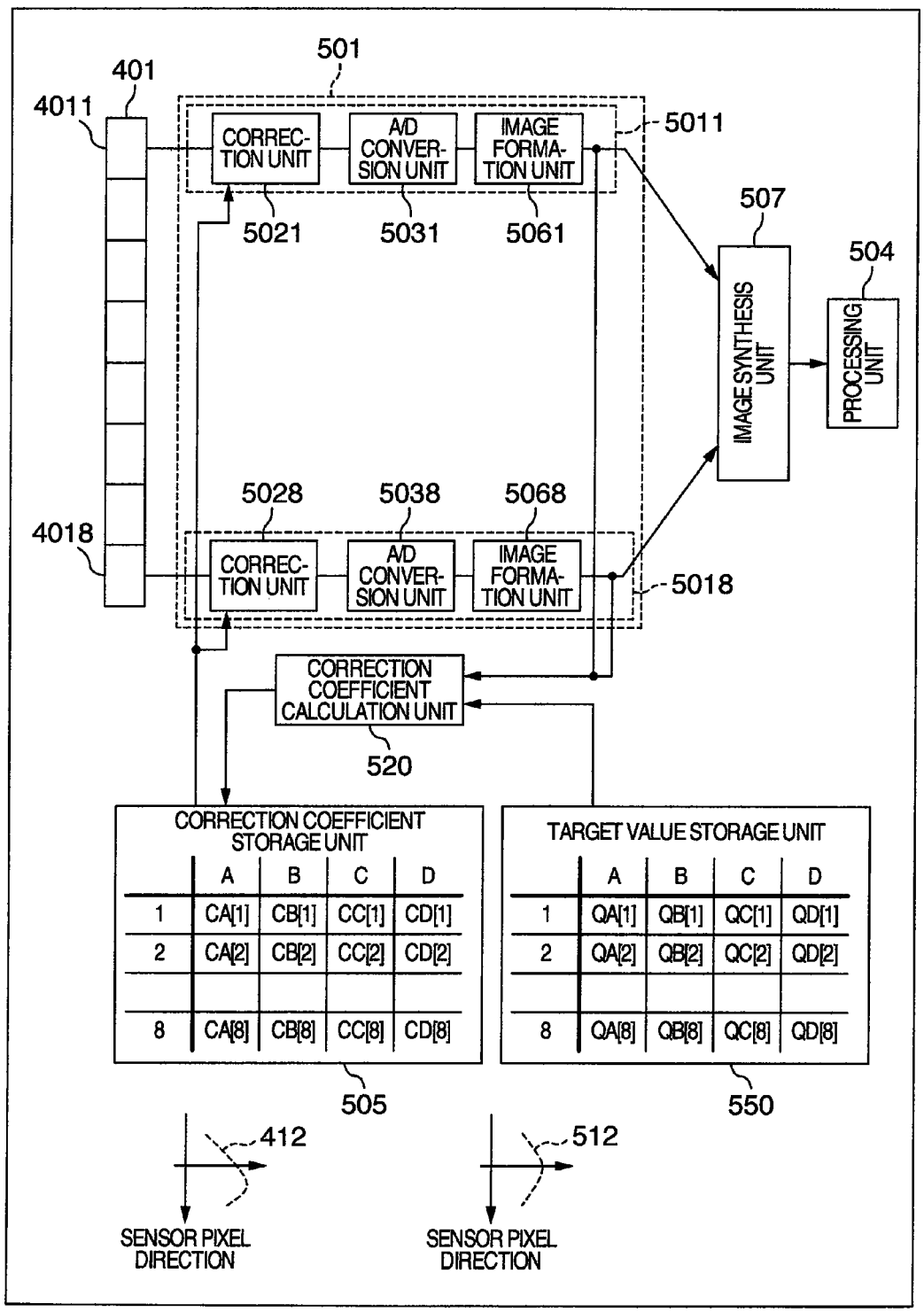
FIG. 3 is a schematic view of portions ranging from a detection system 400 to an image processing system 500 in the embodiment of the invention.

FIG. 3 is a schematic view showing the flow of detection signals from the detection system 400 to the processing system 500.

The light reception surface 401 is constituted by light reception cells that are arranged either one-dimensionally or two-dimensionally and is divided into regions 4011 to 4018.

Distribution 412 of the intensities of the detection signals of the regions 4011 to 4018 does not have a similar shape in a plurality of detection devices owing to variance of constituent elements such as the illumination system 100 and the condensation optical system 200.

The intensity 412 of the detection signal is corrected for each region by each signal correction unit 5021 to 5028 provided individually to each channel and the intensity distribution 512 of the detection signal after correction can be changed to an arbitrary shape by this correction.

Here, the correction units 5021 to 5028 are constituted in such a fashion as to acquire a simple proportional gain.

A correction coefficient storage unit 505 stores a correction coefficient that is different depending on each optical condition and this correction coefficient is set to each correction unit 5021 to 5028 in accordance with the optical condition. In consequence, correction can be made while the change of the optical characteristics in the case where the illumination direction and a magnification ratio are changed is taken into consideration.

The detection signal so corrected is digitized by A/D converters 5031 to 5038 and is imaged by image formation units 5061 to 5068. The images are combined by an image synthesis unit 507 and are transferred to an image processing unit 504.

The image processing unit 504 executes a comparison processing of the images aligned in a scanning direction and inspects an image defect of the inspection object and adhering dust.

Correction by the correction unit described above is brought forth by the correction coefficient shown in FIG. 3. Explanation will be further given on this correction coefficient.

The detection signal of a photo-electric image sensor has a distribution 412 of the output intensity as shown in FIG. 3. The distribution 412 of this output intensity is corrected so as to attain an intensity distribution 512 (distribution having a shape like a curve of the second order describing maximum at the center and minimum at both ends with respect to the arrangement direction of eight photoelectric cells) after correction.

A reference target value of reference signal intensity is inputted by external input means 530 to the target value storage unit 550.

Reference target values QA(1) to QA(8) are allocated to an A column in such a fashion as to correspond to the arrangement of the eight photoelectric cells (channels CH1 to CH8)

and the optical conditions (A, B, C and D). The reference target values are likewise allocated in accordance with other conditions B to D, respectively.

The reference target values of the reference signal intensity have a distribution of a shape analogous to a curve of the second order in which the maximum value exists at the center and the minimum value, at both ends.

The correction coefficient calculation unit 520 calculates a correction coefficient. The correction coefficient so calculated is stored in the correction coefficient storage unit 505. Correction coefficients CA(1) to CA(8) are allocated to the A column in such a fashion as to correspond to the arrangement of the eight photoelectric cells (channels CH1 to CH8) and the optical conditions (A, B, C and D) in the correction coefficient storage unit 505. The correction coefficients are likewise allocated in accordance with other conditions B to D, respectively.

Figure 4:
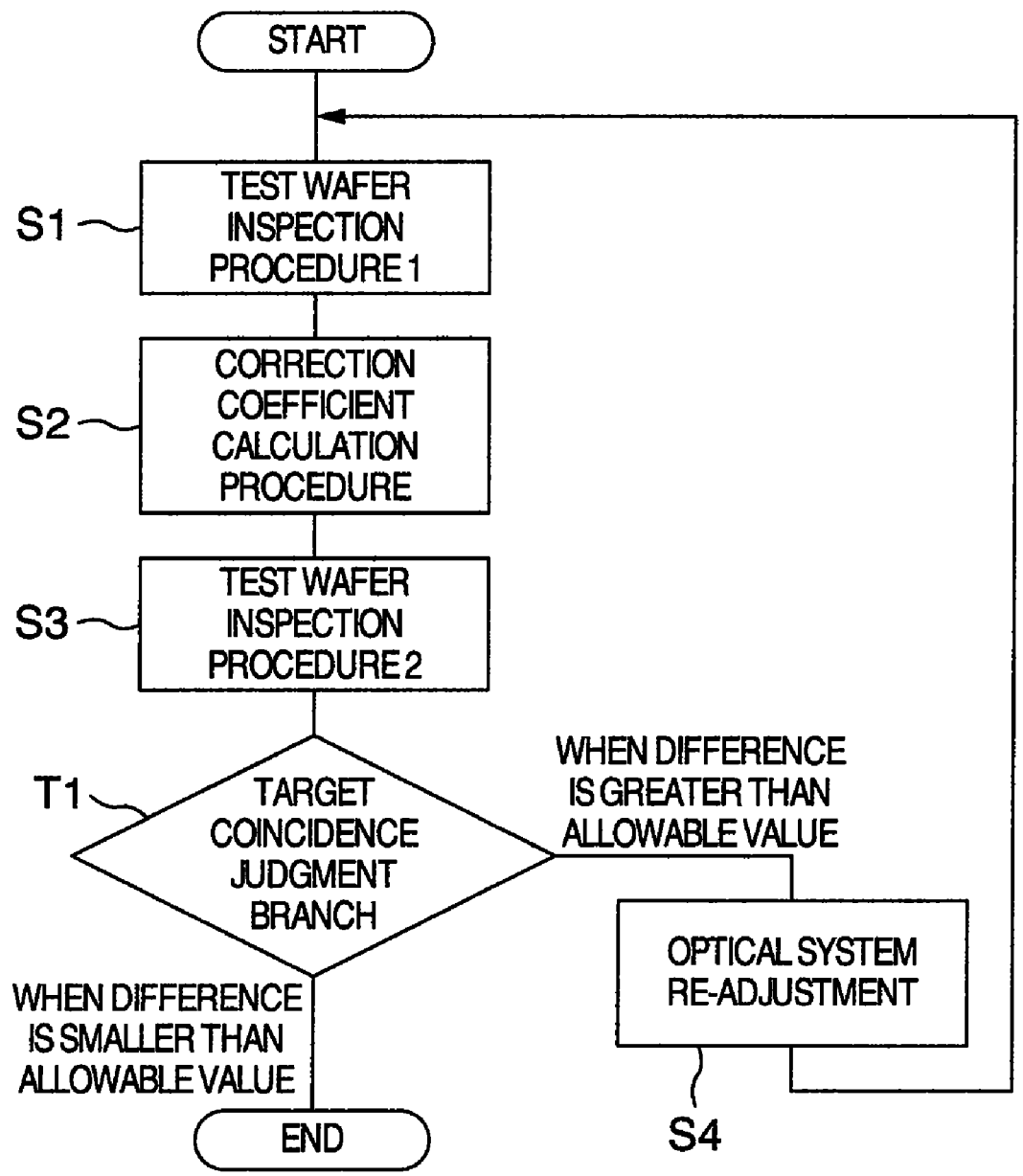
FIG. 4 is a flowchart of a correction coefficient calculation method in the embodiment of the invention.

FIG. 4 is a flowchart showing a correction method according to the embodiment of the invention. This flowchart shows the correction method for keeping performance matching of the inspection sensitivity of each inspection device. The correction coefficient is decided in accordance with the flow shown in FIG. 4 for each optical condition.

Explanation will be given first on the case where correction is made as for the condition A. In step S1 (test wafer inspection procedure 1), an inspection object as a reference (test wafer, in this case) 001 is inspected and the output intensity of the detection image signal for each channel is acquired.

The test wafer hereby used is the one that is prepared by applying PSL (polystyrene latex) to a part or the entire surface of a bare wafer. Alternatively, the test wafer may be a wafer having a uniform reflection factor on its entire surface.

At this time, scattered light from the test wafer 001 for each region is received and the sum of the output for each pixel outputted is defined as the intensity of the detection signal in the region. Alternatively, the sum of luminance inside a search area of each region of the image acquired by the inspection may be defined as the intensity of the detection signal.

The intensity of the detection signal so obtained is expressed as PA1[i] (i: sensor region number).

In this instance, the correction unit 502 does not correct the detection signal and the detection signal obtained itself by the detection system 400 is transferred to the image processing unit 504.

In step S1 (test wafer inspection procedure 1), the intensity QA[i] of the detection signal as the target for each channel, corresponding to the set optical condition, is acquired from the correction coefficient storage unit 505 and the correction coefficient calculation unit 530 calculates the correction function that renders the intensity PA1[i] of the detection signal acquired in step S1 (test wafer inspection procedure 1) coincident with the intensity QA[i] of the target detection signal.

Here, a simple proportion is used as the correction function. That is, CA[i] is used as a coefficient and is set to CA[i]=PA1[i]/AQ[i]. The value CA[i] calculated in this manner is stored in the correction coefficient storage unit 505.

In step S3 (test wafer inspection procedure 3), the correction coefficient CA[i] of the corresponding optical condition (here, optical condition A) is called out from the correction coefficient storage unit 505 and is set to each of the correction units 5021 to 5028.

The test wafer is inspected under this condition and the intensity of the detection signal is acquired. The intensity PA2[i] of the detection signal corrected and the target value QA[i] are compared and correction is finished when the difference of the intensities of the detection image signals of each channel remains within the allowable range.

When the difference exceeding the allowable range exists, the flow proceeds to step S4 (optical system re-adjustment procedure) and readjustment of the optical system such as re-examination of parameters under that optical condition is carried out. The flow then returns again to step S1 and a series of flows is executed.

Incidentally, T1 is a target coincidence judgment branch.

FIGS. 5A to 5D show several examples of the correction target value when correction of the inspection sensitivity of the inspection device is carried out.

The intensity QA[i] of the detection signal on the output side as the target intensity of the detection signal of each channel may well be an arbitrary function by taking into account an illumination intensity distribution depending on the illumination optical system and the detection optical system.

When laser is used as the light source, for example, the intensity may be a secondary function $QA[i]=a(i-c)^2+b$ (a, b and c: real numbers) or a regular distribution when the influences of the intensity distribution and aberration of the lenses of the illumination optical system are collectively taken into account.

Alternatively, it is possible to select a master from among a plurality of applicants and (when correction is carried out under the optical condition A) to set MA[i] of the actual detection signal on the output side to the intensity B[i] of the detection signal as the target. Still alternatively, NA[i] obtained by approximating this detection signal MA[i] on the output side by an arbitrary function may be used.

Figure 5A:
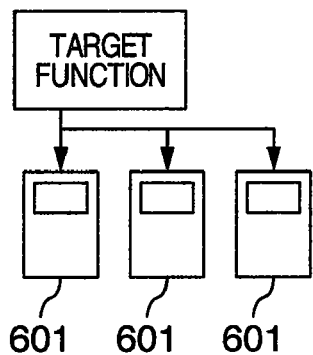
FIGS. 5A to 5D show a management method of a target value in the embodiment of the invention.
Figure 5B:
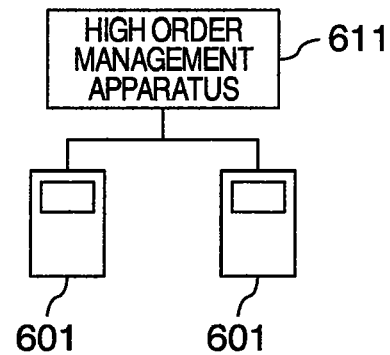

FIGS. 5A to 5D illustrate means for sharing the intensity value QA[i] of the detection signal as the target among a plurality of devices. The intensity QA[i] of the detection signal as the target may be individually acquired by external input means 530 provided to an individual inspection device 601 as shown in FIG. 5A.

Alternatively, it is possible to connect a plurality of inspection devices to a high order management apparatus 611, to store the intensity B[i] of the detection signal as the target in the high order management apparatus 611 and to transfer the intensity B[i] to the individual inspection device when the correction coefficient is calculated.

Still alternatively, the following construction can be employed. Namely, the high order management apparatus 611 has therein a correction coefficient calculation unit 530 and a correction target value storage unit 505. When the correction coefficient is calculated, PA1[i] and PA2[i] of the detection signals on the output side of the individual inspection devices 601 are transferred and calculation of the correction coefficient is executed inside the high order management apparatus 611. The correction coefficient so calculated is transferred to the individual inspection device 601 and is stored in the correction coefficient storage unit 505.

The high order management apparatus may be installed inside the same plant or at a remote place while connected through a network such as the Internet. The number of the high order management apparatus may be either plural or single.

The correction target value QA[i] may be only one kind. Alternatively, different target values may be set at different production sites and may be unified only inside the same place or within a predetermined range.

Figure 5C:
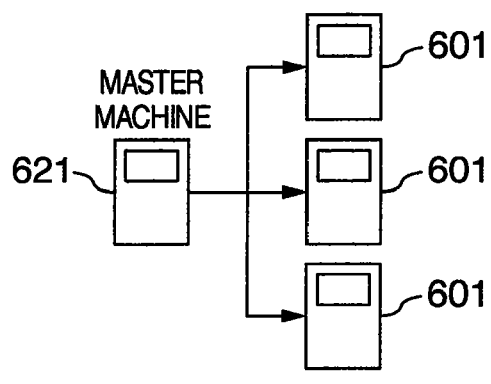

Still alternatively, the correction target value QA[i] may be acquired by setting a master machine 621 from among a plurality of devices as shown in FIG. 5C and may be used as the intensity of the detection signal when the inspection object as the reference is inspected.

Figure 5D:
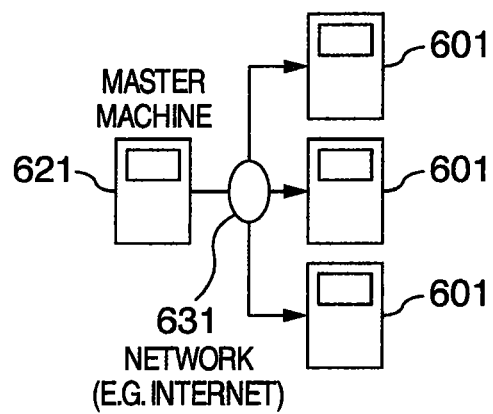

The master machine 621 may be connected through a network such as the Internet as shown in FIG. 5D.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection device for inspecting defects or foreign matters on a surface of an inspection object, comprising:
   a light source for irradiating a luminous flux to said inspection object;
   an optical system for guiding reflected and scattered light reflected from said inspection object;
   a photoelectric image sensor having a plurality of photoelectric cells arranged, for converting said reflected and scattered light guided to electric detection signals;
   a detection signal transfer unit having channels each constituted by a signal correction unit, an A/D converter and an image formation unit, and corresponding to each of a plurality of regions formed by dividing said photoelectric image sensor, respectively; and
   an image synthesis unit for forming an image of the surface of said inspection object by synthesizing partial images outputted by said detection signal transfer unit;
   said inspection device inspecting defects or foreign matters of the surface of said inspection object by processing said synthesized image;
   wherein said detection signal transfer unit has a detection signal correction function capable of bringing a detection signal from said photoelectric cell close to a reference target value of a reference detection signal intensity determined for each of said channels.

2. An inspection device according to claim 1, which further comprises an external input unit for acquiring the reference target value of said reference detection signal intensity from outside.

3. An inspection device according to claim 2, wherein said photoelectric cells are arranged either one-dimensionally or two-dimensionally on coordinates in said photoelectric image sensor.

4. An inspection device according to claim 2, which further comprises:
   a correction coefficient calculation unit for comparing an intensity of the detection signal acquired by inspection of said reference inspection object with an intensity of said reference detection signal and calculating a correction coefficient for bringing the detection signal close to said reference target value, and a correction coefficient storage unit for storing said correction coefficient;
   wherein said correction coefficient of said correction coefficient storage unit is provided to said signal correction function.

5. An inspection device according to claim 4, wherein said correction coefficient calculation unit calculates said correction coefficient for each channel, and said correction coefficient for each channel is stored in said correction coefficient storage unit.

6. An inspection device according to claim 1, wherein correction by said detection signal correction function is carried out under a plurality of optical conditions of said optical system.

7. An inspection device according to claim 4, wherein calculation of said correction coefficient is made either periodically or non-periodically by said correction coefficient calculation unit.

8. An inspection method for an inspection device for inspecting defects or foreign matters on a surface of an inspection object, said inspection device including:
   a light source for irradiating a luminous flux to an inspection object;
   an optical system for guiding reflected and scattered light reflected from said inspection object;
   a photoelectric image sensor having a plurality of photoelectric cells arranged, for converting said reflected and scattered light guided to electric detection signals;
   a detection signal transfer unit having channels each constituted by a signal correction unit, an A/D converter and an image formation unit, and corresponding to each of a plurality of regions formed by dividing said photoelectric image sensor; and
   an image synthesis unit for forming an image of the surface of said inspection object by synthesizing partial images outputted by said detection signal transfer unit;
   said inspection device inspecting defects or foreign matters of the surface of said inspection object by processing said synthesized image;
   wherein said detection signal transfer unit is corrected in such a fashion as to bring the detection signal from said photoelectric cell close to a reference target value of a reference detection signal intensity determined for each channel.

9. An inspection method according to claim 8, wherein the reference target value of said reference detection signal intensity is acquired from outside.

10. An inspection method according to claim 9, wherein an inspection device further includes a correction coefficient calculation unit for comparing an intensity of the detection signal acquired by inspection of said reference inspection object with an intensity of said reference detection signal and calculating a correction coefficient for bringing the detection signal close to said reference target value, and a correction coefficient storage unit for storing said correction coefficient, and said correction coefficient of said correction coefficient storage unit is provided to said signal correction function.

11. An inspection method according to claim 10, wherein said correction coefficient calculation unit calculates said correction coefficient for each channel, and said correction coefficient for each channel is stored in said correction coefficient storage unit.

12. An inspection method according to claim 11, wherein correction by said detection signal correction function is carried out under each of a plurality of optical conditions of said optical system.

13. An inspection method according to claim 10, wherein calculation of the correction coefficient is made either periodically or non-periodically by said correction coefficient calculation unit.

14. An inspection method according to claim 8, which can execute a transmission processing of transmitting the reference target value of said detection signal intensity and a detection signal obtained by the inspection of a reference inspection object as a reference target value to other inspection devices.

15. An inspection device according to claim 1, wherein said reference target value of said reference detection signal intensity has a distribution like a curve of the second order which attains a maximum value at a center of a channel and a minimum value at both ends.

16. An inspection device according to claim 1, wherein each of said channels of said detection signal transfer unit has a correction unit, an A/D converter and an image formation device arranged in the order named from the input side of the detection signal, and the detection signal is corrected by gain adjustment of said correction unit bearing said detection image signal correction function.

* * * * *